US008771228B2

(12) United States Patent
Butterfield

(10) Patent No.: US 8,771,228 B2
(45) Date of Patent: Jul. 8, 2014

(54) IV PUMP ADAPTED FOR GENERIC TUBING

(75) Inventor: Robert D. Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 245 days.

(21) Appl. No.: 12/986,092

(22) Filed: Jan. 6, 2011

(65) Prior Publication Data

US 2012/0179131 A1 Jul. 12, 2012

(51) Int. Cl.
*A61M 5/145* (2006.01)
(52) U.S. Cl.
USPC ............................. 604/151; 417/478; 417/479
(58) Field of Classification Search
USPC ............ 604/67, 131, 151, 153; 417/478, 479
See application file for complete search history.

(56) References Cited

U.S. PATENT DOCUMENTS

| 4,345,594 A * | 8/1982 | Bisera et al. ..................... 604/69 |
| 4,617,014 A | 10/1986 | Cannon et al. |
| 5,018,945 A * | 5/1991 | D'Silva .......................... 417/12 |
| 5,125,891 A | 6/1992 | Hossain et al. |
| 5,658,252 A * | 8/1997 | Johnson ........................ 604/131 |
| 2003/0069559 A1 | 4/2003 | Platt et al. |

FOREIGN PATENT DOCUMENTS

EP 0429866 6/1991

OTHER PUBLICATIONS

International Search Report and Written Opinion for PCT/US2012/020114 mailed Jul. 30, 2012 in 10 pages.

* cited by examiner

*Primary Examiner* — Quynh-Nhu H Vu
(74) *Attorney, Agent, or Firm* — McDermott Will & Emery LLP

(57) ABSTRACT

A system and method of accurately pumping a fluid using tubing of variable inner diameter and material is disclosed. The disclosed pump comprises a pumping mechanism configured to compress and release a portion of a flexible tube to cause fluid to flow along the flexible tube, a gauging apparatus, and a vacuum apparatus. The gauging apparatus is configured to determine the inner diameter of the flexible tube, which value is used in calibrating the pumping rate of the pump. The vacuum apparatus is configured to reduce the ambient pressure in a volume surrounding the portion of the flexible tube, thereby causing the flexible tube to fully expand to its original outside diameter when the flexible tube is released by the pumping mechanism.

8 Claims, 11 Drawing Sheets

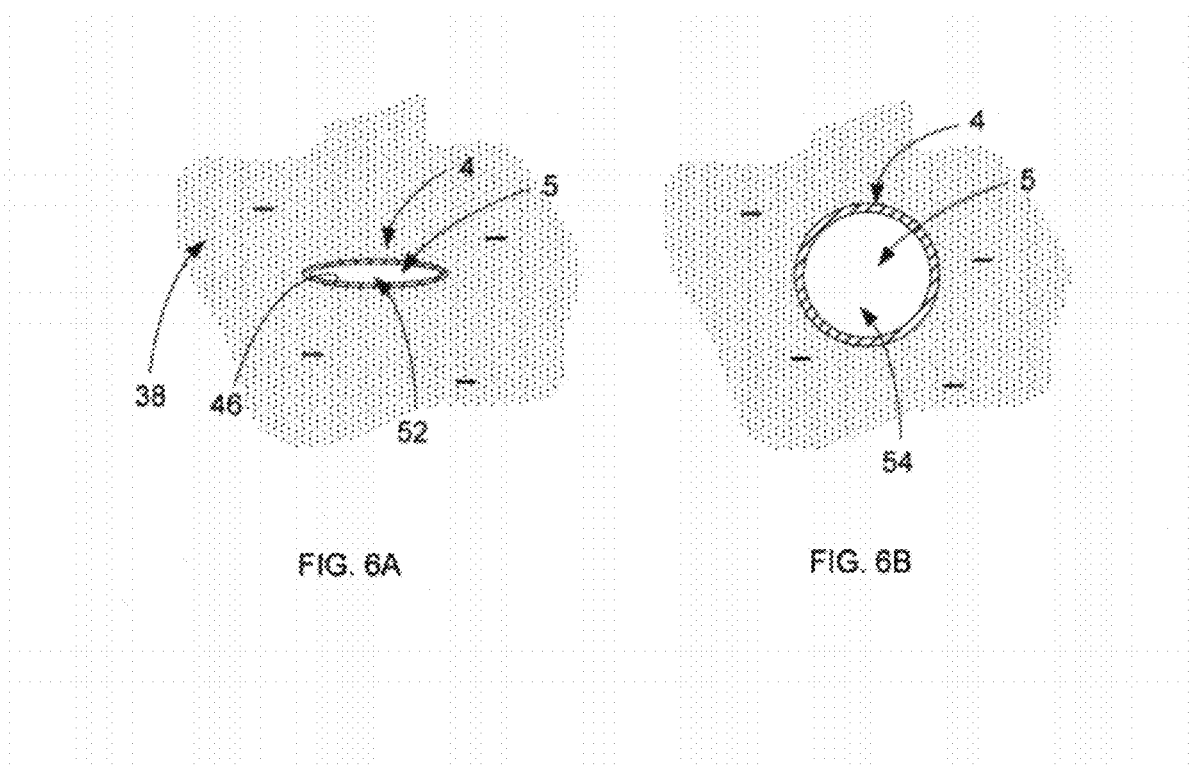

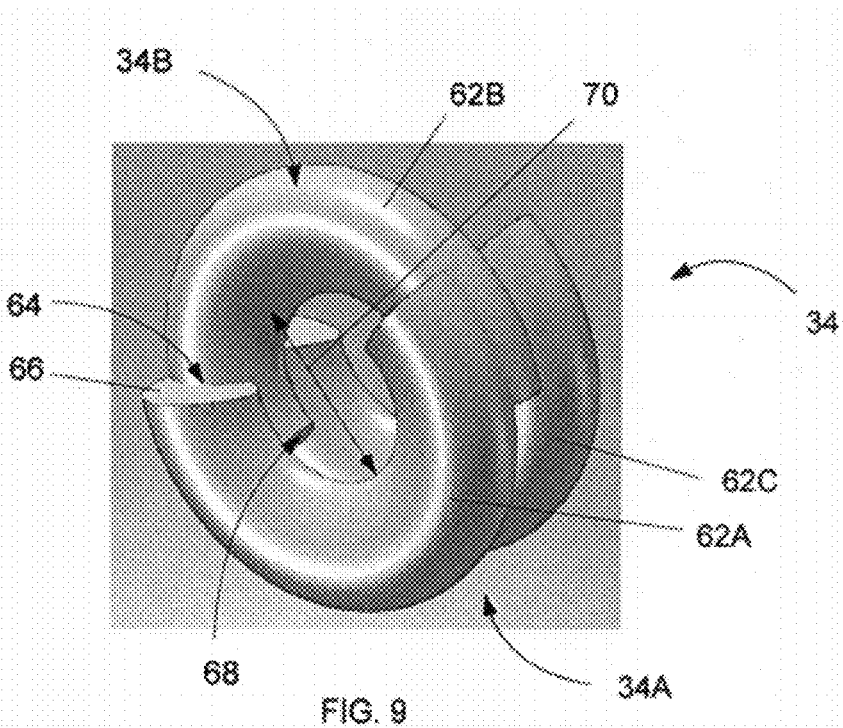
FIG. 9
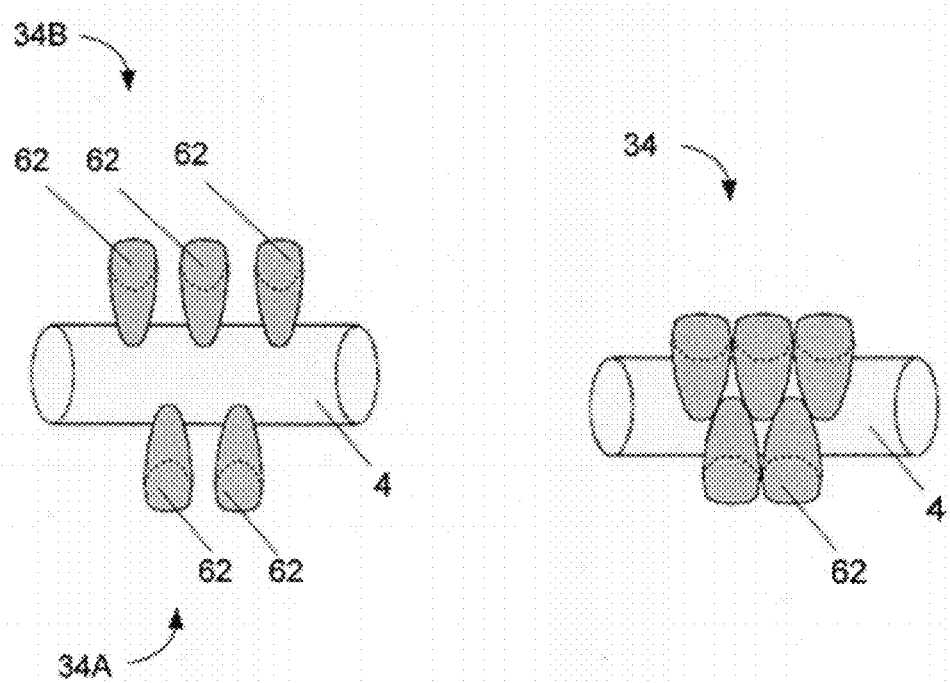
FIG. 10A
FIG. 10B

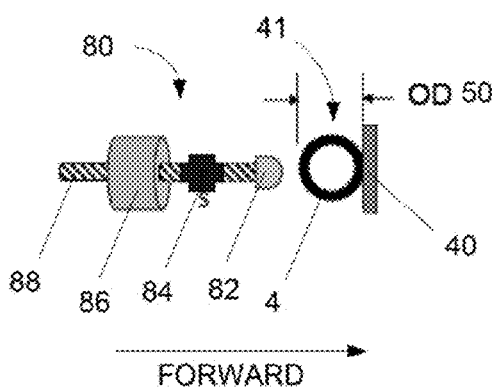
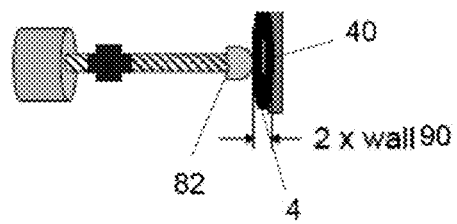
FIG. 11A    FIG. 11B
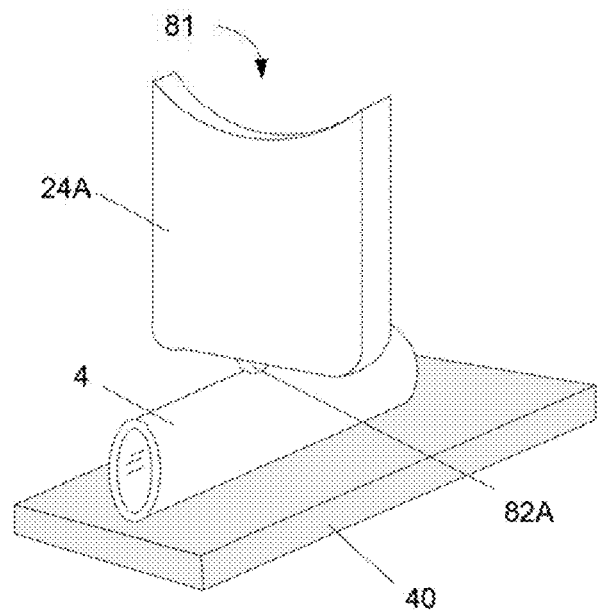
FIG. 11C

IV PUMP ADAPTED FOR GENERIC TUBING

BACKGROUND

1. Field

The present disclosure generally relates to systems and methods of pumping intravenous (IV) fluids, and, in particular, relates to IV pumps adapted to use tubing having an unknown diameter and/or insufficient recovery of the uncompressed shape.

2. Description of the Related Art

Infusion pumps have become commonplace within the healthcare world as a way to precisely administer intravenous (IV) fluids. Use of a pump in place of a simple roller clamp with an elevated fluid container to control the flow of the IV fluid allows more accurate and consistent control of the rate of delivery of the fluid to a patient.

The assembly of drip chamber, tubing, valves, fittings, and Luer fittings that connect the fluid container to the patient may be referred to as an "IV set." IV sets designed for use with IV pumps may have a pumping segment or chamber incorporated into the set, wherein the pumping segment fits into a compartment in the IV pump, as shown in FIG. 1. In use, medical fluid passes from the IV fluid container 14 through the tubing of IV set 18 to a infusion needle inserted in the arm of patient 10. The IV set 18 passes through a pumping module 20 of IV pump 12 that contains actuators (not shown) that act upon the pumping segment under the control of control unit 16 to force the medical fluid to flow to the patient 10 at a specified rate.

One of the factors that affect the accuracy of the pumping rate of a peristaltic IV pump is the inside diameter of the tubing of the IV set. A second factor is the material of the tubing, wherein the tubing must fully recover its uncompressed shape between compressions so that the tube refills to the maximum volume. Precision IV sets having tubing made from a highly resilient material and with precise control of the inside diameter may be both expensive and, in some areas, difficult to obtain. There is, therefore, a desire for IV pumps to be able to use "generic" tubing, i.e. tubing that does not have precision control of the inner and/or outer diameter or may be made of a material that takes a compression "set" and does not fully return to the uncompressed shape.

SUMMARY

In order to provide an accurate rate of delivery of fluid using a peristaltic pump while using generic tubing, it is advantageous to provide a system that automatically measures the tubing as well as fully expanding the tubing between compression strokes. The system and method disclosed herein provide at least some of these advantages.

A pump is disclosed that comprises a pumping mechanism configured to compress and release a portion of a flexible tube to cause fluid to flow along the flexible tube, a gauging apparatus, and a vacuum apparatus. The gauging apparatus is configured to determine the inner diameter of the flexible tube, thereby calibrating the pumping rate of the pump. The vacuum apparatus is configured to reduce the ambient pressure in a volume surrounding the portion of the flexible tube, thereby causing the flexible tube to fully expand when released by the pumping mechanism.

A pump is disclosed that comprises a pumping mechanism configured to compress and release a portion of a flexible tube to cause fluid to flow along the flexible tube, and a vacuum apparatus that is configured to reduce the ambient pressure in a volume surrounding the portion of the flexible tube, thereby causing the flexible tube to fully expand when released by the pumping mechanism.

A pump is disclosed that comprises a pumping mechanism configured to compress and release a portion of a flexible tube to cause fluid to flow along the flexible tube, and a gauging apparatus configured to determine an inner diameter of the flexible tube, thereby calibrating the pumping rate of the pump.

A method of accurately pumping fluid using a flexible tube of unknown inner diameter is disclosed, wherein the method comprises the step of placing a flexible tube in a pump such that a portion of the flexible tube is coupled to a pumping mechanism, wherein the pumping mechanism is configured to manipulate the portion of the flexible tube to cause fluid to flow along the flexible tube. The pump automatically measures an outside diameter of the flexible tube, and then compresses the flexible tube until an inner wall of the internal channel makes contact with the inner wall on an opposite side of the internal channel and measures a residual thickness of the compressed flexible tube. From these measurements, the pump calculates the inner diameter of the flexible tube by subtracting the residual thickness from the outer diameter and automatically adjusting the operating parameters of the pumping mechanism to pump fluid at a specific rate.

A method of accurately pumping fluid using a flexible tube of unknown inner diameter is disclosed, wherein the method comprises the step of placing a flexible tube in a pump such that a portion of the flexible tube is coupled to a pumping mechanism, wherein the pumping mechanism is configured to manipulate the portion of the flexible tube to cause fluid to flow along the flexible tube. The pump then forms a sealed vacuum enclosure around the pumping mechanism and the portion of the flexible tubing and reduces the pressure within the vacuum enclosure. The pump then activates the pumping mechanism to manipulate the portion of the flexible tube.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 6A-6B illustrate the function of a vacuum in expanding a flexible tube according to certain aspects of the present disclosure.

FIG. 9 depicts an exemplary split seal according to certain aspects of the present disclosure.

FIG. 10A illustrates details of construction of the split seal of FIG. 1 according to certain aspects of the present disclosure.

FIG. 10B illustrates details of operation of the split seal of FIG. 1 according to certain aspects of the present disclosure.

FIGS. 11A-11B depict an exemplary gauging apparatus according to certain aspects of the present disclosure.

FIG. 11C depicts another embodiment of a gauging apparatus according to certain aspects of the present disclosure.

DETAILED DESCRIPTION

The disclosed methods and system provide a pumping system that is able to accurately pump fluid using a flexible tube that may have unknown inner and/or outer diameters or may be made of a material that does not have the resilience to fully recover its uncompressed shape between compressions or may take a compression set after some period of use.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The methods and systems disclosed herein are presented in terms of administration of a medical fluid as an infusion by a nurse in a healthcare environment. It will be apparent to one of ordinary skill in the art that the same methods and systems, however, may be used in other areas of fluid handling and pumping. Nothing in this disclosure should be interpreted, unless specifically stated as such, to limit the application of any method or system disclosed herein to a healthcare environment.

Figure 1:
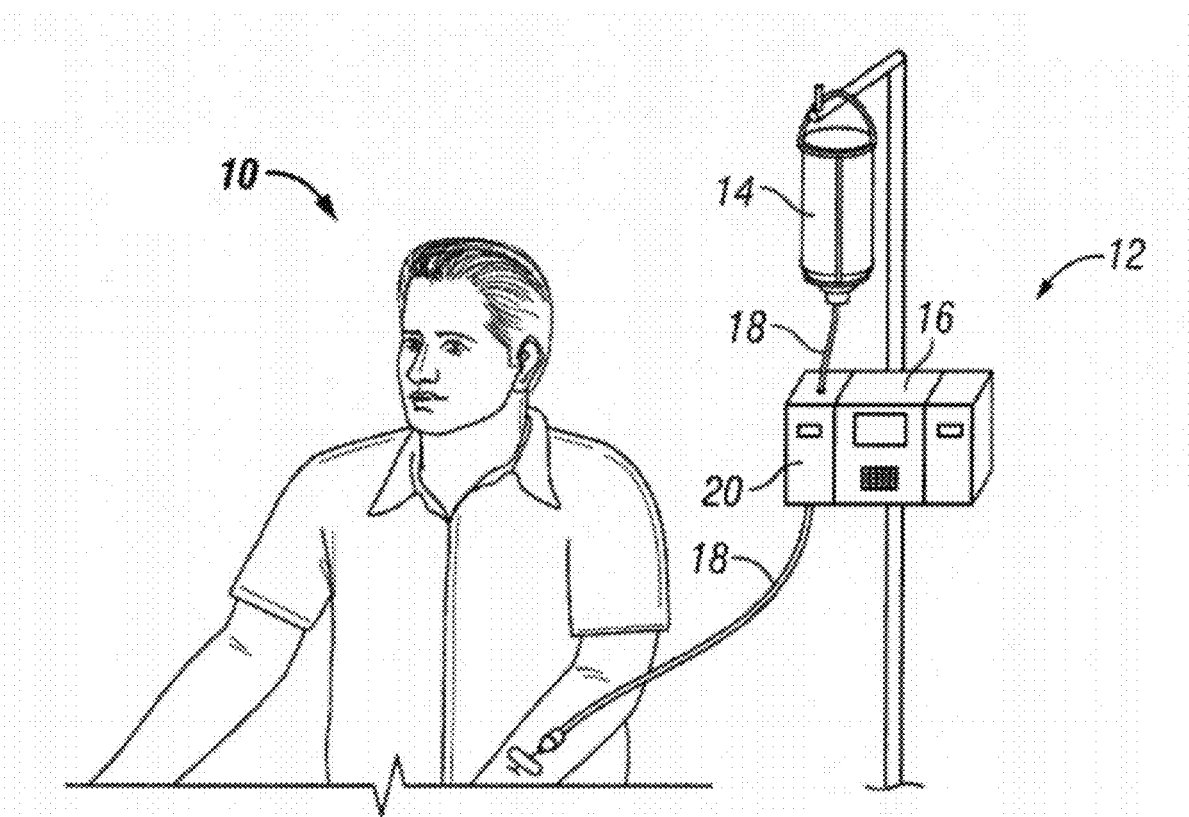
FIG. 1 depicts a patient receiving medical fluid through an IV set using an IV pump.

FIG. 1 depicts a patient 10 receiving medical fluid through an IV set 18 using an IV pump 12. The fluid is provided, in this example, in a flexible container 14 that is commonly hung above the pump 12 to provide a positive pressure at the pump inlet. The IV pump 12 shown herein has a control unit 16 and an attached pumping module 20. The IV set 18 connects the fluid container 14 to the patient 10, and passes through the pumping module 20. The flow rate of the medical fluid is volumetrically controlled by the positive displacement pumping action of pumping module 20 under the control of control unit 16.

Figure 2:
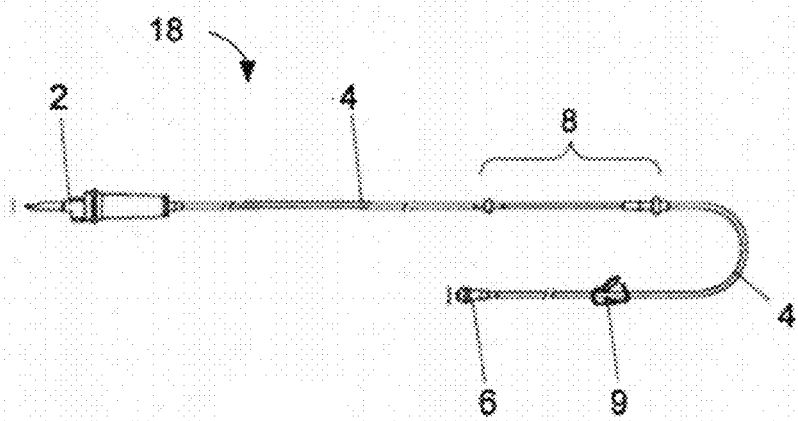
FIG. 2 depicts the construction of an IV set according to the prior art.

FIG. 2 depicts the construction of a IV set 18 according to the prior art. This IV set 18 is set up for use with a peristaltic pump and the pumping segment that fits into the peristaltic pump is the length of tubing and fitting indicated by bracket 8. A special material such as silicone rubber or a highly plasticized polyvinyl chloride (PVC) is commonly used to form this segment. These materials are used to provide high dimensional stability and resilience to restore to their undeformed shape when not contacted by the positive displacement mechanism and thus ensure accuracy from set to set and over the duration of use of a single set. A length of flexible tube 4 is attached to each end of the pumping segment 8. A container spike 2 is attached to the other end of one length of flexible tube 4, wherein a container spike 2 is a standard IV fitting configured to attach to a IV container 14 and puncture a seal that is part of the connection fitting on the IV container 14. An alternate connection is a needleless Luer fitting or other type of fluid connector adapted for connection to a fluid source. At the other end of the other length of flexible tube 4, in this example, is a needleless Luer connector 6 that is suitable for connection to an infusion needle, such as shown in FIG. 1. In certain embodiments, other types of connectors and devices are attached in place of Luer connector 6. Also shown is a clamp 9 that, when closed completely, blocks flow through the flexible tube 4 to which the clamp 9 is attached. This is frequently used to prevent flow and spillage while setting up or removing a IV set 18 from a pump. In certain embodiments, other types of fitting and connectors are added to create a multitude of other configurations of IV sets, depending on the application and type of treatment.

Figure 3A:
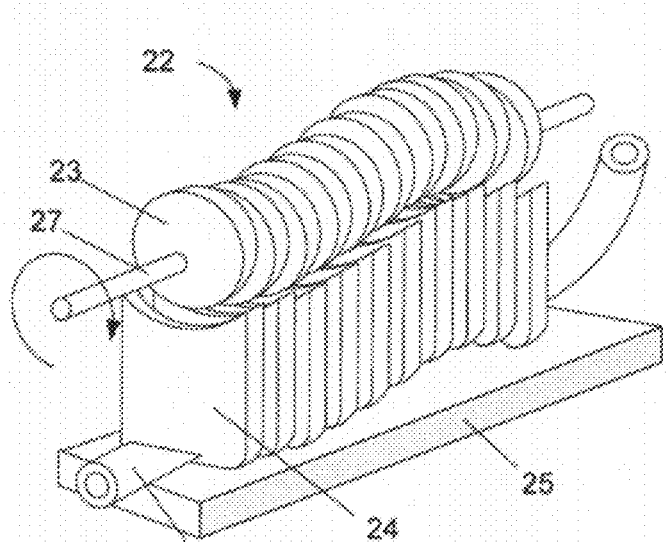
FIG. 3A depicts the construction of a peristaltic pumping mechanism according to the prior art.

FIG. 3A depicts the construction of a peristaltic pumping mechanism 22 according to the prior art. A series of cams 23 are arranged along a shaft 27 such that the orientation of the cams are incrementally displaced between adjacent cams. Each cam 23 has an associated cam follower 24 that moves "up" and "down", in the orientation of FIG. 3A, as the cam 23 rotates. A portion of a flexible tube 4 is placed over platen 25 and under the cam followers 24. The spacing of the cam followers 24 and the platen 25 is selected such that the cam follower 24 fully compresses the flexible tube 4 when the cam follower 24 is in the fully extended or "down" position.

Figure 3B:
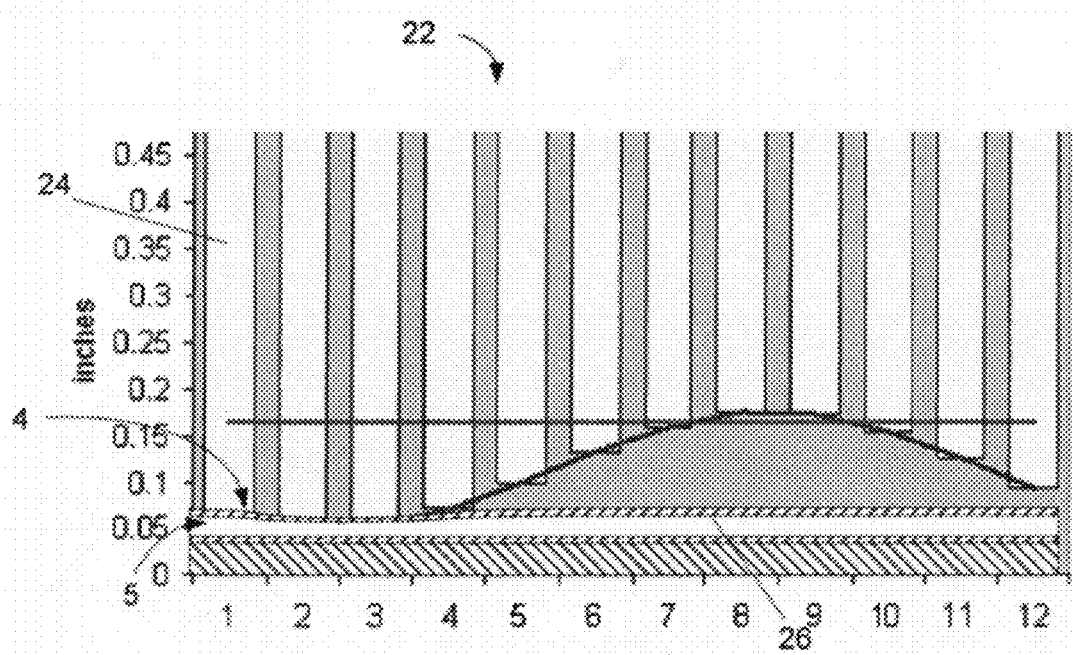
FIG. 3B depicts the operation of the peristaltic pumping mechanism of FIG. 3A.

FIG. 3B schematically depicts the operation of the peristaltic pumping mechanism 22 of FIG. 3A. As the shaft 27 of FIG. 3A rotates, each cam follower 24 moves up and down, in the orientation of FIG. 3B, as controlled by the associated cam 23. It can be seen in FIG. 3B that a volume 26 is formed within the internal channel 5 of tube 4 by the two cam followers 24 that are fully extended, or "down", thereby pinching the tube 4 together. The incrementally offset orientations of cams 23 causes a wave-like motion to ripple through the cam followers 24, which causes the volume 26 to move along the length of flexible tube 4. As each of the cam followers 24 retracts into the "up" position, the flexible tube 4 recovers and expands. The materials of typical precision IV sets are commonly selected to have a high resilience such that the tube 4 fully and repeatably expands to the maximum cross-section during this recovery, ensuring accurate volumes 26 as they are formed and carried along the pumping mechanism 22. If a flexible tube 4 does not fully recover its undeformed shape, the volume 26 is reduced and the pumping accuracy is also reduced. As materials that have the necessary level of resilience to fully recover between compressions tend to be more expensive than other materials, IV sets made from this resilient material will tend to be higher in cost than they would be if made from non-resilient materials. Chemical plasticizers are added to some tubing materials to increase their resilience, however there is a recognized clinical concern around the potential for some of these chemicals to reach the patient.

Figure 4:
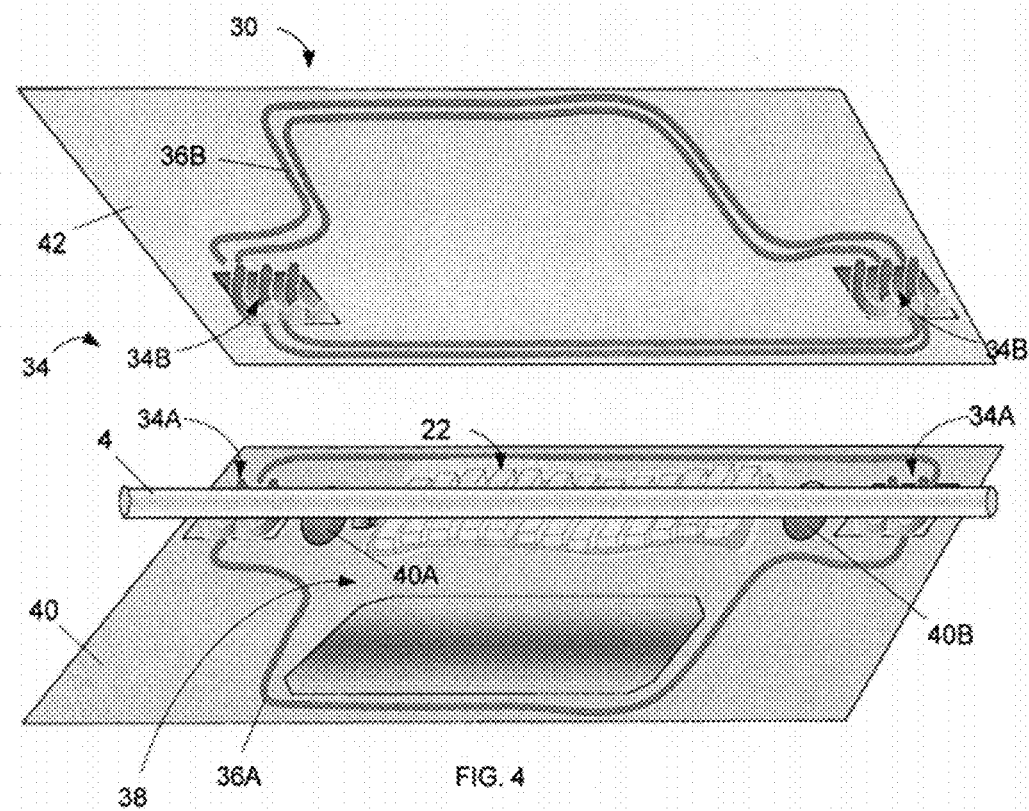
FIG. 4 depicts a vacuum apparatus that provides a vacuum around the pumping mechanism constructed according to certain aspects of the present disclosure.

FIG. 4 depicts a vacuum apparatus 30 that provides a vacuum around the pumping mechanism 22 constructed according to certain aspects of this disclosure. The IV pump 12 includes a pumping mechanism 22 that is configured to manipulate a portion of flexible tube 4 to cause fluid to flow along the flexible tube 4. In the example of FIG. 4, the portion of flexible tube 4 is a straight segment across a multi-element pumping mechanism 22. In other embodiments using other types of peristaltic pumping mechanisms 22, such as a roller on a rotating arm, the portion of flexible tube 4 may be circular or follow another non-straight path.

The vacuum apparatus 30 comprises a fixed panel 40 and a movable panel 42 that are, in this example, hingedly connected (not shown connected in FIG. 4) and have perimeter seals 36A and 36B configured to seal to each other when the movable panel 42 is moved into contact with the fixed panel 40. There are two split seals 34 located at positions along the perimeter seals 36A, 36B, wherein each split seal 34 has a split seal segment 34A that is coupled to the fixed panel 40 and a split seal segment 34B that is coupled to the movable panel 42. The split seal segments 34A and 34B are in contact with each other when the movable panel 42 is in contact with fixed panel 40 and form a seal around flexible tube 4. The combination of the perimeter seals 36A, 36B and the split seals 34 provide an airtight seal between the fixed panel 40 and a movable panel 42 such that a vacuum can be created within the vacuum enclosure 38. The split seal 34 is discussed in more detail with respect to FIGS. 8 and 9A-9B. The split seal may be formed as a contiguous portion of a membrane covering the pumping fingers and thus assuring no leakage of air via the pumping finger mechanism. The IV pump 12 also includes, in this example, two pressure sensors 40A and 40B upstream and downstream of the pumping mechanism 22 that are used to detect problems such as occlusions in the flexible tube 4 and depletion of the source of the fluid.

Figure 5:
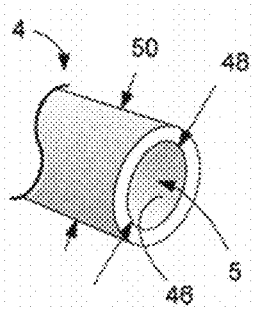
FIG. 5 depicts a portion of a flexible tube that is used with the disclosed IV pump according to certain aspects of the present disclosure.

FIG. 5 depicts a portion of a flexible tube 4 that is used with the disclosed IV pump 12 according to certain aspects of this disclosure. Flexible tube 4 is, in this example, circular in cross-section with an outside diameter 50 and has an internal channel 5 with an internal wall 46, wherein the internal channel 5 has an inner diameter 48.

FIGS. 6A-6B illustrate the function of a vacuum in expanding a flexible tube 4 according to certain aspects of this disclosure. The internal channel 5 of the flexible tube 4 has a pressure that, for the purpose of this example, is considered to be ambient pressure. In some embodiments, this pressure may be lower if the fluid source 14 is below the pump 12, thereby creating a negative pressure head within the tubing at the elevation of the IV pump 12. In current IV pumps, this would result in some collapse of the tubing 4. In the vacuum enclosure 38 that surrounds the flexible tube 4, a reduced pressure has been created, wherein the reduced pressure is below the pressure inside internal channel 5. In FIG. 6A, the flexible tube 4 is partially compressed and the internal channel 5 has a cross-section area 52. The difference between the pressure within the internal channel 5 and the reduced pressure outside of the flexible tube 4 create a uniform force on the internal wall 46 that tends to force the flexible tube 4 to expand to maximize the area of the cross-section of the internal channel, as shown in FIG. 6B, wherein internal channel 5 has a cross-section area 54 that is larger than area 52 of the partially flattened flexible tube 4 of FIG. 6A. Cross-section area 54 is maximized when the flexible tube 4 assumes a circular profile, which is considered to be the natural circular geometric configuration of flexible tube 4.

Figure 7A:
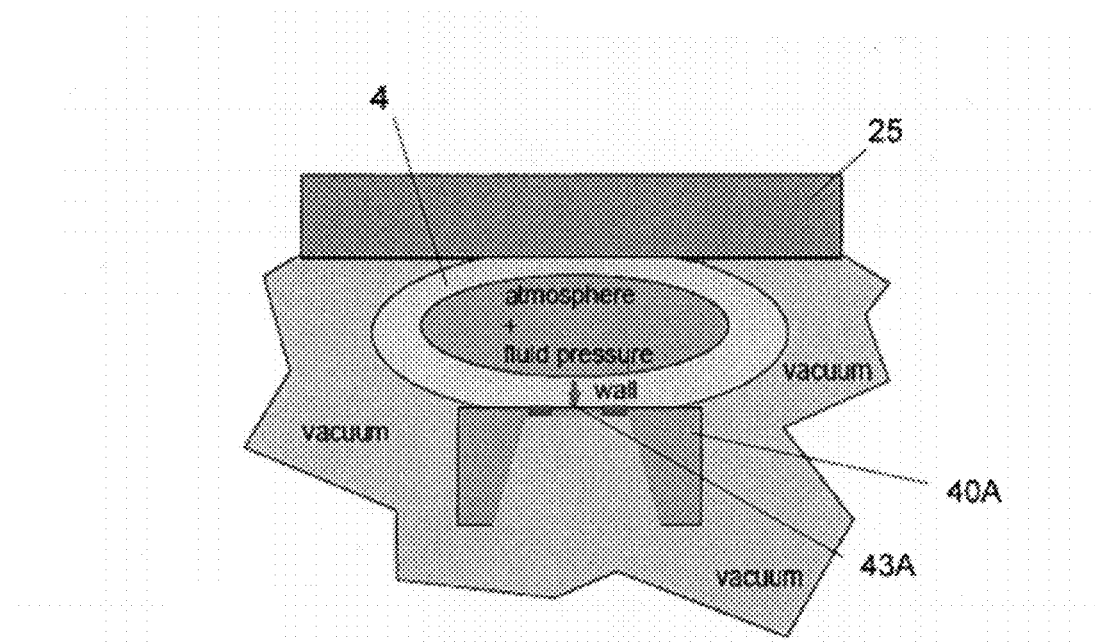
FIGS. 7A-7B depict close-up cross-sections of pressure sensors according to certain aspects of the present disclosure.
Figure 7B:
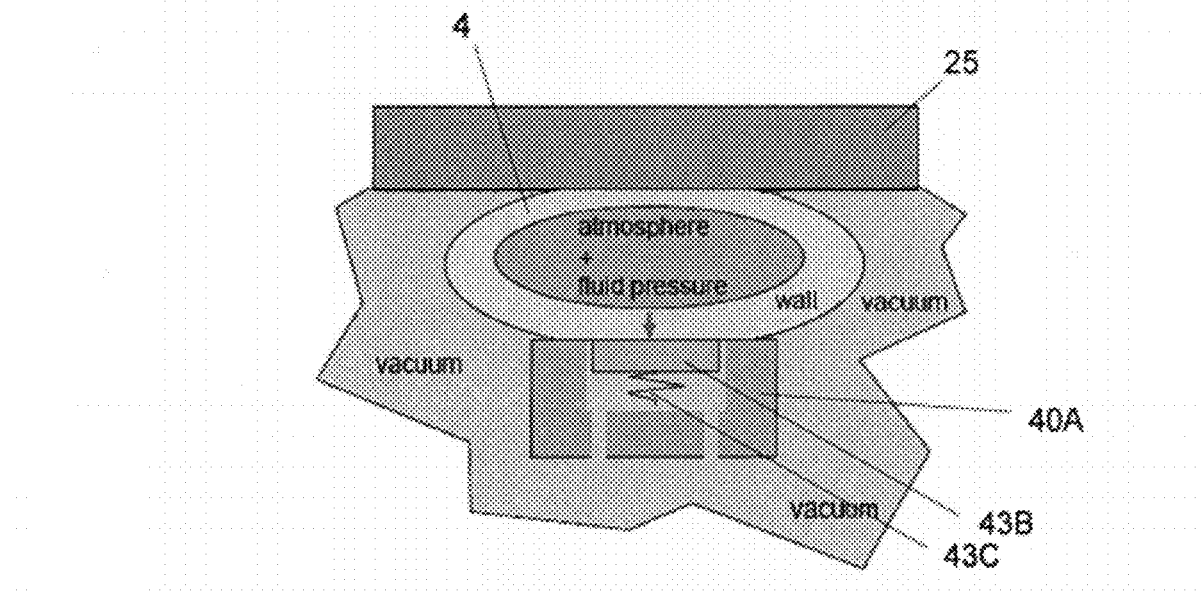

FIGS. 7A-7B depict close-up cross-sections of pressure sensors 40A, 40B according to certain aspects of the present disclosure. The pressure sensors 40A, 40B are really 'force sensors' which measure the sum of tube wall force and fluid force. The design of the force sensors may take further advantage of the presence of the vacuum. Conventionally there must be sufficient wall force present to maintain the wall of the tube 4 in contact with the sensors 40A, 40B. This is needed when the sensor 40A, 40B must detect negative pressures as when the pump 12 is higher than the patient 10 or in the intake pathway to detect an occlusion between the container 14 and the pump 12. With the vacuum design, there need not be ANY wall force present and yet the tube will still attempt to expand and thus can be trapped between the sensor 40A, 40B and the platen 25 as shown in FIGS. 7A and 7B. FIG. 7A shows a sensor 40A that senses the deflection of a flexible element 43A to measure the force. FIG. 7B uses a moving element 43B mounted on a spring 43C and measures the displacement of the moving element 43B, which correlates with the force. By reducing the need for wall force, a preferred tube 4 design may be chosen with either a thin wall or a highly elastic wall, similar to a fire hose. With this tube 4, the accuracy of the sensors 40A, 40B is increased due to less uncertainty in the magnitude of the wall force which typically changes over time as tubes 4 visco-elastically deform. Note also that the sensors 40A, 40B must measure the gauge vacuum pressure, i.e. below ambient atmosphere, in order to accurately convert the sensed force to a pressure.

Figure 8:
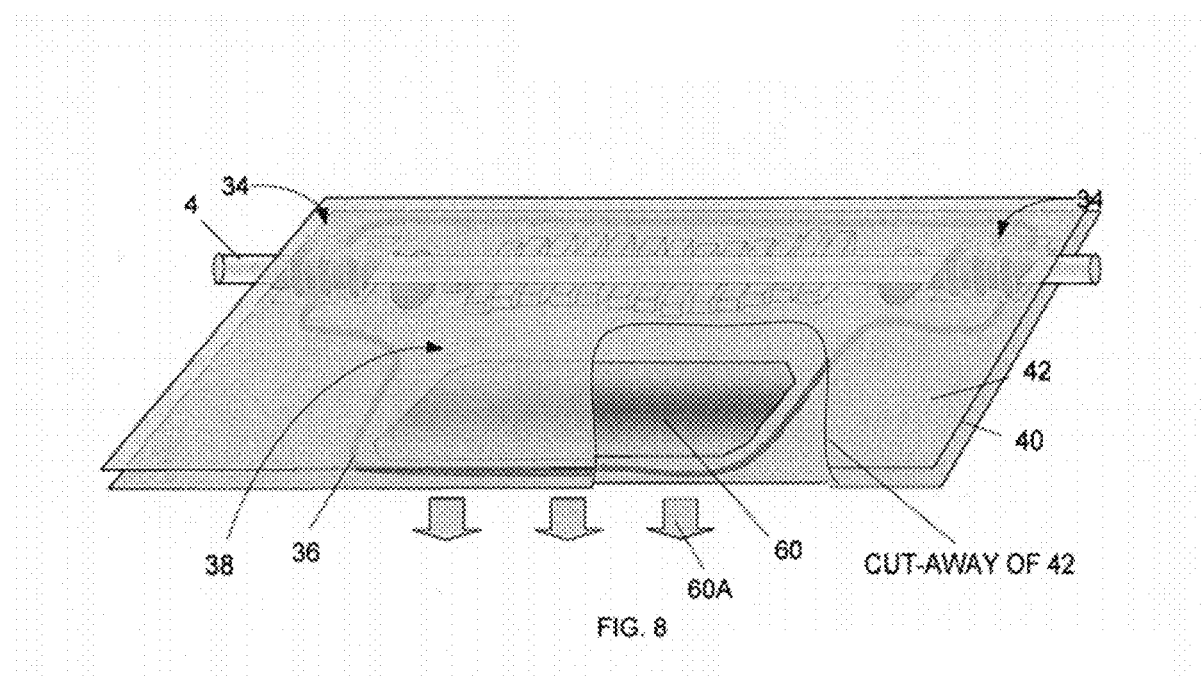
FIG. 8 depicts the vacuum enclosure of FIG. 4 in the closed position according to certain aspects of the present disclosure.

FIG. 8 depicts the vacuum apparatus 30 of FIG. 4 in the closed position according to certain aspects of this disclosure. Movable panel 42 has been rotated from its open position as shown in FIG. 4 to be in contact with fixed panel 40. Vacuum enclosure 38 has a perimeter formed around pumping mechanism 22 by cooperation of perimeter seals 36A, 36B and split seals 34A, 34B surrounding the flexible tube 4 at the points where flexible tube 4 crosses the perimeter seal 36A, 36B.

In the cutaway depiction of movable panel 42, an exemplary vacuum mechanism 60 can be seen. Vacuum mechanism 60 reduces the air pressure within the vacuum enclosure 38, in this example, by deforming a flexible panel formed within the fixed panel 40, wherein the deformation expands the volume of the vacuum enclosure 38. This expansion is indicated by the arrows 60A. As the amount of air within the vacuum enclosure 38 is fixed, expansion of the volume of the vacuum enclosure 38 causes a reduction in the air pressure within the vacuum enclosure 38. In certain embodiments, the deformable panel of vacuum mechanism 60 is actuated mechanically as the movable panel 42 is rotated against fixed panel 40. In certain embodiments, the deformable panel of vacuum mechanism 60 is actuated by a manual lever (not shown). In certain embodiments, the deformable panel of vacuum mechanism 60 is actuated by a solenoid or motor (not shown). In other embodiments, the pressure of the air within the vacuum enclosure 38 is reduced by withdrawing air from the vacuum enclosure 38 using an air pump (not shown). In certain embodiments, a check valve (not shown) is positioned such that air can be drawn through the check valve by a cyclic pumping mechanism (not shown).

FIG. 9 depicts an exemplary split seal 34 according to certain aspects of this disclosure. The split seal, in this example, is formed from 3 partial o-rings 62A, 62B, and 62C. Partial o-rings 62A and 62C are a part of a split seal segment such as the split seal segment 34A of FIG. 4, while partial o-ring 62B is a part of a matching split seal segment similar to split seal segment 34B. In the embodiment of FIG. 8, partial o-ring 62B is positioned between partial o-rings 62A and 62C and in contact with both partial o-rings 62A and 62C in lateral areas 64, forming a bore 68 through the complete split seal 34. Bore 68 has an inner diameter 70 that is, in this example, slightly smaller than the outer diameter 50 of flexible tube 4. In certain embodiments, the seals are sufficiently adaptable to accommodate a range of tubing diameters, for example 0.12-0.17 inches outer diameter (OD). The partial o-rings 62A-62C are formed, in this example, from a soft elastomer that deforms around the flexible tube 4 to form a continuous seal around the outside of flexible tube 4. In certain embodiments, the partial o-rings 62 are configured such that pairs of opposing partial o-rings 62, e.g. partial o-rings 62A and 62B, are aligned and sized such that they contact each other on cut surfaces 66. In certain other embodiments, the partial o-rings 62 have a rectangular cross-section that provides a larger contact area to each other and to flexible tube 4 compared to a circular cross-section. In certain other embodiments, the split seal segments 34A and 34B comprise more or fewer partial o-rings than shown in FIG. 9. In certain other embodiments, an additional fitting (not shown) is placed around the flexible tube, conceptually similar to the ferrules used to seal rigid metal tubing to plumbing fittings, at the time of placement of the flexible tube 4 in IV pump 12 to provide improved sealing.

FIG. 10A illustrates details of construction of the split seal 34 of FIG. 1 according to certain aspects of this disclosure. Split seal segment 34A, in this embodiment, comprises two partial o-rings 62 and split seal segment 34B comprises three partial o-rings 62. The partial o-rings 62 are configured such that they interlock when split seal segments 34A and 34B are brought together.

FIG. 10B illustrates details of operation of the split seal 34 of FIG. 1 according to certain aspects of this disclosure. Split seal segments 34A and 34B have been brought together around a flexible tube 4. It can be seen that there is a continuous seal is formed around the flexible tube 4 by the partial o-rings 62.

FIGS. 11A-11B depict an exemplary gauging apparatus 80 according to certain aspects of this disclosure. Flexible tube 4 is, in this example, positioned in location 41 against the fixed panel 40. The gauging apparatus 80 comprises a tip 82 mounted on a shaft 88, wherein the shaft 88 includes a force sensor 84. The tip 82 is moved forward, i.e. toward the flexible tube 4, by the action of actuator 86. In certain embodiments, shaft 88 is threaded and constrained from rotating, and actuator 86 comprises a rotating nut (not shown) that causes the shaft 88 to move axially as the rotating nut turns. In FIG. 11A, the tip 82 is moved forward until the tip 82 contacts the flexible tube 4. The distance between the tip 82 and the fixed panel 40 is the outer diameter 50 of flexible tube 4. This measurement of the gauging apparatus 80 can be calibrated by touching tip 82 directly to the fixed panel 40 when the flexible tube 4 is not present. In certain embodiments, tip 82 comprises a detector (not shown) that senses contact between the tip 82 and flexible tube 4. In certain embodiments, this measurement is taken only after the pressure around flexible tube 4 has been reduced to fully expand the flexible tube 4.

The vacuum created around the tube 4 by the vacuum apparatus 30 of FIG. 4 works cooperatively with the gauging apparatus 80 of FIG. 11A. The vacuum encourages the tube 4 to assume a circular profile, as the internal pressure within tube 4 seeks to reach the most expanded configuration. This enhances the reliability of a single diameter measurement to be representative of the true fully expanded diameter of tube 4.

In FIG. 11B, the gauging apparatus 80 is configured to measure the wall thickness of the flexible tube 4. The tip 82 has been moved forward until the flexible tube 4 is collapsed and the distance 90 between tip 82 and fixed panel 40 is twice the thickness of the wall of flexible tube 4. In certain embodiments, the distance 90 at which the internal surfaces 46 of flexible tube 4 touch can be sensed by the force sensor 84 as the force will begin to increase as a much higher rate after the walls come into contact. The inner diameter 48 can therefore be calculated by subtracting the measurement 90 from the measured OD 50 as shown:

ID=OD−(2×wall)          (1)

FIG. 11C depicts another embodiment of a gauging apparatus 81 according to certain aspects of the present disclosure. In this embodiment, the tip 82 is attached to a force sensor (not visible in FIG. 11C) inside one of the cam followers 24A. The cam follower can be moved in the same manner as the actuator 86 of FIG. 11A, moving the cam follower 24A forward until the tip 82A touches the tube 4.

Figure 12:
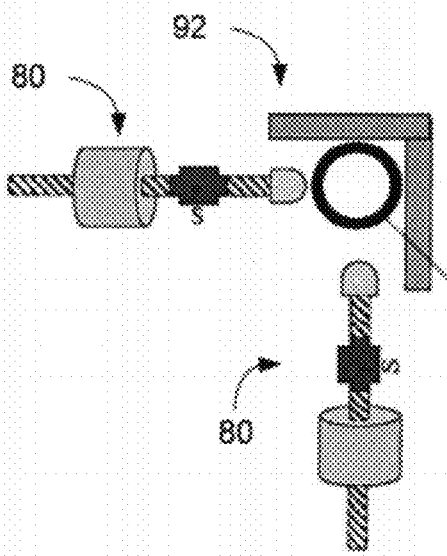
FIG. 12 depicts another embodiment of a gauging apparatus according to certain aspects of the present disclosure.

FIG. 12 depicts another embodiment of a gauging apparatus 92 according to certain aspects of this disclosure. This embodiment employs two gauges 80 to measure the outside diameter 50 in two perpendicular directions to compensate for any out of round condition of flexible tube 4. When the tips of both probes are both advanced until the tips touch the flexible tube 4, similar to the situation shown in FIG. 11A, then the two measurements will compensate for the flexible tube 4 not being truly round as is assumed in the measurement configuration of FIG. 11A. The system of FIG. 12 is more accurate but more complex than the system of FIG. 11A.

Figure 13:
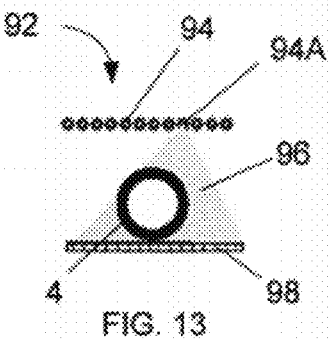
FIG. 13 depicts another embodiment of a gauging device according to certain aspects of the present disclosure.

FIG. 13 depicts another embodiment of a gauging device 92 according to certain aspects of this disclosure. In this embodiment, an array of light-emitting devices 94 is positioned on one side of flexible tube 4 while an array of light-detecting devices 98 is positioned on the opposite side of flexible tube 4 and parallel to the light-emitting array 94. In this embodiment, a single light emitting device 94A is activated and projects a beam 96. Some of the light-detecting devices 98 will detect the beam 96 while flexible tube 4 blocks the beam from reaching others of the light-detecting devices 98. Other light emitting devices 94 will be individually activated until the beam 96 reaches light-detecting devices 98 on both sides of flexible tube 4, whereupon the diameter of flexible tube 4 is calculated using knowledge of the geometry of the gauging device 92 and the positions of the light-emitting device and the light-detecting devices that are receiving the beam 96.

Figure 14:
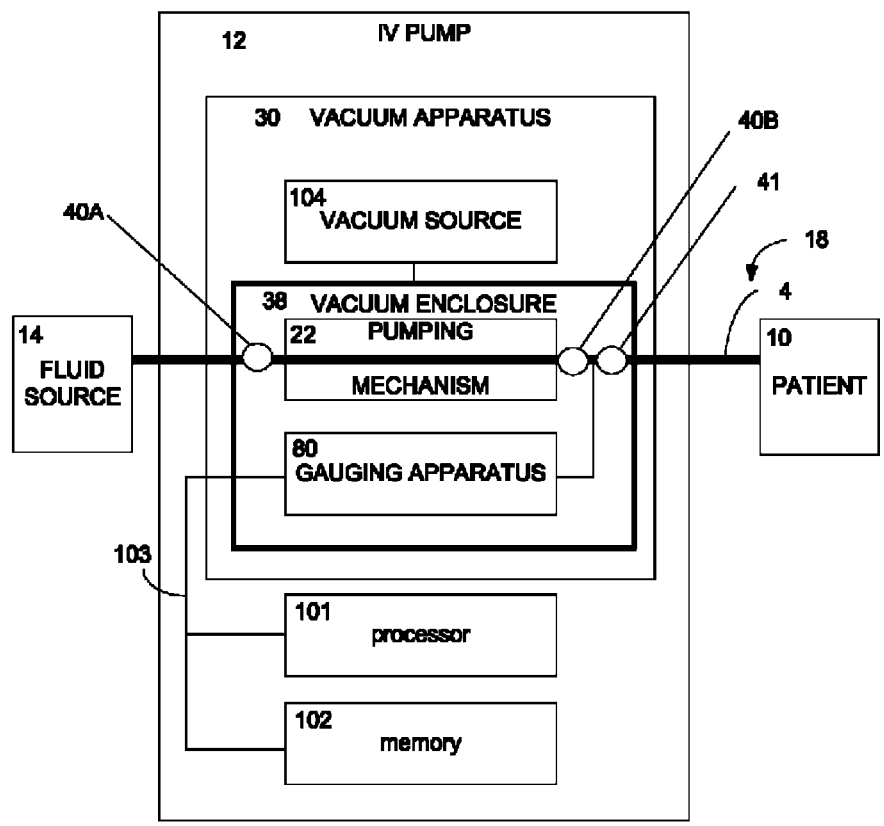
FIG. 14 is a block diagram of an exemplary IV pump with a vacuum apparatus and a gauging apparatus according to certain aspects of the present disclosure.

FIG. 14 is a block diagram of an exemplary IV pump 12 with a vacuum apparatus 30 and a gauging apparatus 80 according to certain aspects of this disclosure. An IV set 18 is coupled between a source of medical fluid 14 and a patient 10 with a portion of the flexible tube 4 of IV set 18 passing through pumping mechanism 22. Vacuum enclosure 38 encompasses pumping mechanism 22. A vacuum source 104 is connected to the vacuum enclosure 38. In this example, a gauging apparatus 80 is contained within the vacuum enclosure 38 and coupled to the flexible tube 4 such that the gauging apparatus 80 measures, in this example, the OD 50 and compressed thickness 90 of the flexible tube 4 and provides an uncompressed ID of the flexible tube 4. In certain embodiments, the gauging apparatus 80 is outside the vacuum enclosure 38. The vacuum apparatus 30 also includes pressure sensors 40A, 40B and an air-in-line sensor 41 that are located within the vacuum enclosure 38. The IV pump 12 comprises a processor 101 that is coupled to a memory 102 that is configured to store executable instructions and data and to the gauging apparatus 80 through a network 103, wherein the processor 101 retrieves executable instructions that are stored in the memory 102, accepts an input of a selected flow rate, receives signals comprising the uncompressed ID from the gauging apparatus 80, and calculates the ID of the flexible tube 4. In certain other embodiments, the processor 101, memory 102, and gauging apparatus 80 are interconnected by any of a variety of methods known to those of ordinary skill in the art, such as a RS-232 serial communication link and a direct parallel bus link.

Figure 15:
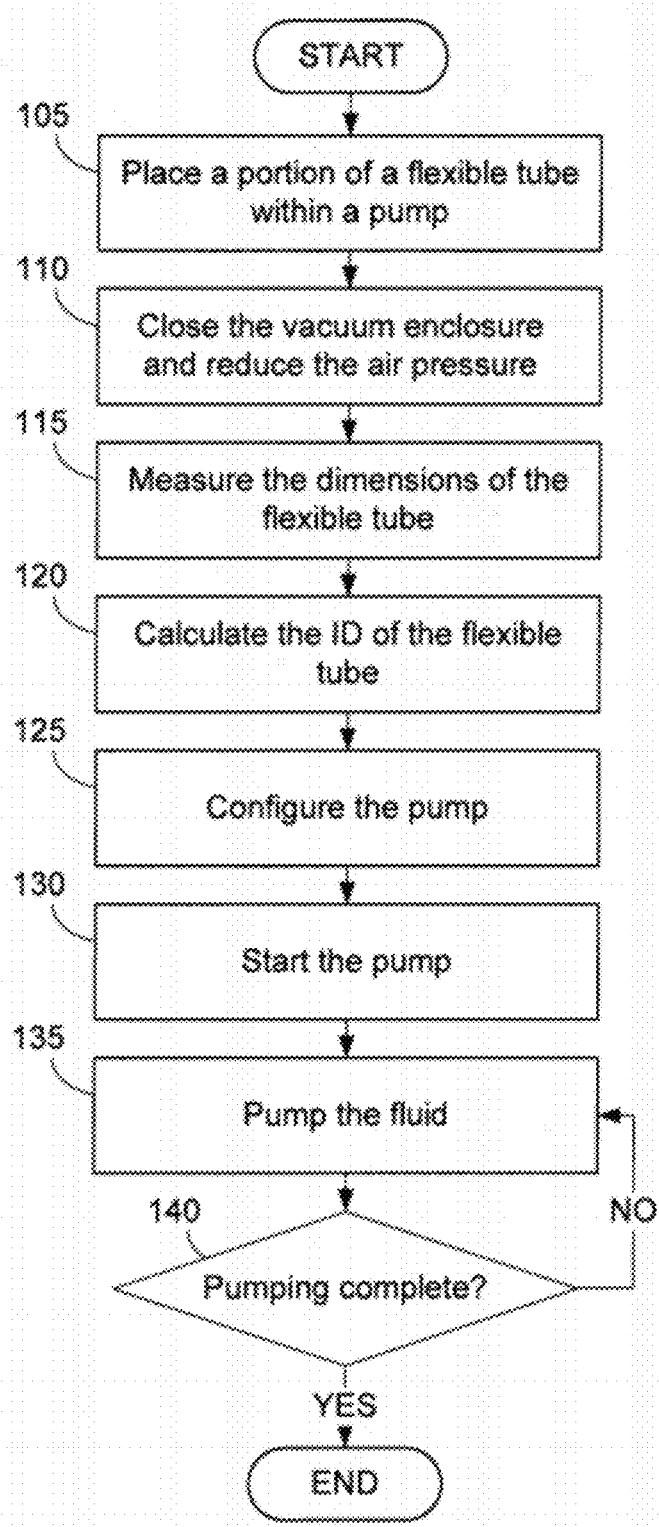
FIG. 15 is a flow chart illustrating an exemplary method of pumping a fluid according to certain aspects of the present disclosure.

FIG. 15 is a flow chart illustrating an exemplary method of pumping a fluid according to certain aspects of this disclosure. Starting in step 105, the user connects a flexible tube 4 to a source of fluid 14 and places a portion of the flexible tube 4 within a pump 12 that comprises a pumping mechanism 22 that is configured to manipulate the portion of the flexible tube 4 to pump the fluid. In step 110, the user closes the vacuum enclosure 38 of the pump 12 around the pumping mechanism 22 and reduces the air pressure within the vacuum enclosure 38. The pump 12 also comprises a gauging apparatus 80 that measures, in this example, the OD 50 and the compressed thickness 90 of the flexible tube 4 in step 115 and, in step 120, a processor 101 that coupled to the gauging apparatus 80 takes the signals from the gauging apparatus and calculates the ID 48 of the flexible tube 4. In certain embodiments, the pumping mechanism has a rate of operation that is associated with tubing having an uncompressed ID and the selected flow rate and the processor adjusts the rate of operation of the pumping mechanism by the ratio of the square of the uncompressed ID to the square of the uncompressed ID received from the gauging apparatus. The processor 101 then configures the pump 12 in step 125 to accurately pump fluid with this particular flexible tube 4 having an ID 48. The user starts the pump in step 130 and continues to operate the pump in step 135. This continues until the pumping is complete, whereupon the decision block 140 branches along the "YES" path to the end. If the pumping is not complete, the decision block 140 branches along the "NO" path back to step 135 and continues to pump fluid.

In summary, systems and methods of accurately pumping fluids using peristaltic pumps and flexible tubes of unknown inner diameter and material are disclosed. By creating an enclosure having a reduced air pressure around the flexible tube, the tube is urged to fully expand between compression cycles of the peristaltic pumping mechanism by the pressure differential between the fluid inside the flexible tube and reduced pressure outside the flexible tube. By automatically gauging the outside diameter and the wall thickness of the flexible tube, the inside diameter of the tube can be calculated, enabling the pump to be calibrated to accurately pump with the particular tubing in use. Together, these systems and methods enable IV pumps that comprise theses system and methods to accurately deliver IV fluids using "generic" tubing, i.e. tubing where the ID is not precisely controlled to a specific value and the tubing material may not be sufficiently resilient to return to the fully expanded shape on its own.

These same methods and systems may be applied to other types of pumps and devices besides peristaltic pumps applying compression to lengths of the tubing that have been used as examples herein. For example, an IV pump that manipulates a hemispherical pumping chamber formed in a cassette that is part of an IV set may employ the vacuum apparatus to fully expand the pumping chamber or employ the gauging apparatus to measure the actual height of the pumping chamber. Similarly, other types of devices such as a flow meter may be improved by utilization of the gauging apparatus as knowledge of the precise inner diameter of the tubing through which the fluid is flowing.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A pump comprising:
    a pumping mechanism configured to compress and release a portion of a flexible tube having an uncompressed inner diameter (ID) to cause a fluid to flow along the flexible tube;
    a gauging apparatus configured to determine the uncompressed ID of the flexible tube;
    and
    a vacuum apparatus configured to reduce the ambient pressure in a volume surrounding the portion of the flexible tube, to thereby assist in expanding the flexible tube to the uncompressed ID when the flexible tube is released by the pumping mechanism, the vacuum apparatus comprising:
- a vacuum enclosure surrounding the pumping mechanism, the vacuum enclosure having a fixed panel and a movable panel, wherein the movable panel has a perimeter that separably seals to the fixed panel when the movable panel is coupled to the fixed panel;
- first and second split seals located on the perimeter of the movable panel, the split seals comprising first and second segments that are configured such that when the movable panel is separated from the fixed panel, the first and second seals open to allow the flexible tube to be installed across the first segment of the first seal, the pumping mechanism, and the first segment of the second seal, the seals configured such that the first and second segments of each seal forms a circumferential seal around the flexible tube when the movable panel is in contact with the fixed panel; and
- a vacuum source coupled to the vacuum enclosure, the vacuum source configured to reduce ambient pressure within the vacuum enclosure when the movable panel is coupled to the fixed panel.

2. The pump of claim 1, wherein the pump is an intravenous (IV) pump configured to accept a disposable IV set for administering an infusion of a medical fluid to a patient, wherein the flexible tube is a component of the IV set.

3. The pump of claim 2, further comprising:
- a memory configured to store executable instructions and data; and
- a processor coupled to the memory, the gauging apparatus, and the pumping mechanism, the processor configured to retrieve the executable instructions and data from the memory, receive the uncompressed ID from the gauging apparatus, accept an input of a selected flow rate, and operate the pumping mechanism, wherein the processor adjusts the operation of the pumping mechanism according to the uncompressed ID to provide the selected flow rate.

4. The pump of claim 3, wherein:
- the pumping mechanism has a rate of operation that is associated with tubing having an uncompressed ID and the selected flow rate; and
- the processor adjusts the rate of operation of the pumping mechanism by the ratio of the square of the uncompressed ID of the tubing to the square of the uncompressed ID received from the gauging apparatus.

5. The pump of claim 4, wherein the pumping mechanism, the gauging apparatus, and the vacuum apparatus are configured to accept a tube having an outside diameter (OD) within a range and an unknown ID, and wherein the gauging apparatus and processor are configured to automatically determine the uncompressed ID of the accepted tube and operate the pumping mechanism to provide the selected flow rate.

6. The pump of claim 1, wherein the gauging apparatus comprises:
- a location configured to accept the flexible tube having an outer diameter (OD) and an internal channel with an inner wall; and
- a gauge configured to:
  - measure the uncompressed OD of the flexible tube and provide a signal comprising the OD measurement; and
  - compress the flexible tube until the inner wall of a side of the internal channel makes contact with the inner wall on an opposite side of the internal channel, measure a residual wall thickness of the compressed flexible tube, and provide a signal comprising the residual wall thickness measurement.

7. The pump of claim 6, wherein the pump further comprises:
- a memory configured to store executable instructions and data; and
- a processor coupled to the memory and the gauges, the processor configured to retrieve the executable instructions from the memory, receive the signals comprising the OD measurement and the residual wall thickness measurement, and calculate the uncompressed ID of the flexible tube by subtracting the residual wall thickness measurement from the outer diameter measurement.

8. The pump of claim 1, wherein the gauging apparatus comprises a force sensor that is coupled to a cam follower.

* * * * *